(12) United States Patent
Okada

(10) Patent No.: US 9,795,278 B2
(45) Date of Patent: Oct. 24, 2017

(54) HOUSING WATERTIGHT MECHANISM AND ENDOSCOPE

(71) Applicant: OLYMPUS CORPORATION, Hachioji-shi, Tokyo (JP)

(72) Inventor: Takeshi Okada, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/288,283

(22) Filed: Oct. 7, 2016

(65) Prior Publication Data

US 2017/0020368 A1   Jan. 26, 2017

Related U.S. Application Data

(63) Continuation of application No. PCT/JP2015/073384, filed on Aug. 20, 2015.

(30) Foreign Application Priority Data

Aug. 22, 2014  (JP) .................................. 2014-169772

(51) Int. Cl.
*A61B 1/00*   (2006.01)
*G03B 17/08*   (2006.01)
(Continued)

(52) U.S. Cl.
CPC ............ *A61B 1/00064* (2013.01); *A61B 1/00* (2013.01); *A61B 1/00009* (2013.01);
(Continued)

(58) Field of Classification Search
CPC ................................................ A61B 1/00064
See application file for complete search history.

(56) References Cited

U.S. PATENT DOCUMENTS

| 6,213,541 B1* | 4/2001 | Razgunas ............ B62D 25/081 296/192 |
| 2009/0225159 A1* | 9/2009 | Schneider .......... A61B 1/00124 348/82 |

(Continued)

FOREIGN PATENT DOCUMENTS

JP   2012-047884 A   3/2012

OTHER PUBLICATIONS

Nov. 17, 2015 International Search Report issued in Patent Application No. PCT/JP2015/073384.

*Primary Examiner* — Clayton E Laballe
*Assistant Examiner* — Dennis Hancock
(74) *Attorney, Agent, or Firm* — Oliff PLC

(57) ABSTRACT

A housing watertight mechanism includes, a case member, a lid member configured to be fixed to the case member, an annular elastic member interposed between a first edge portion and a second edge portion, and compressed in an attaching and detaching direction to fill a space between the first edge portion and the second edge portion when the lid member is fixed to the case member, a first portion formed in the elastic member, and a second portion formed in the elastic member, disposed on a side on which the space between the first edge portion and the second edge portion is broadened when the elastic member is compressed in the attaching and detaching direction, and having a larger size in the attaching and detaching direction than a size of the first portion in the attaching and detaching direction.

4 Claims, 10 Drawing Sheets

(51) Int. Cl.
*A61B 1/005* (2006.01)
*A61B 1/015* (2006.01)
*A61B 1/018* (2006.01)
*A61B 1/04* (2006.01)
*A61B 1/06* (2006.01)
*G02B 23/24* (2006.01)
*G03B 37/00* (2006.01)

(52) U.S. Cl.
CPC ........ *A61B 1/00045* (2013.01); *A61B 1/0057* (2013.01); *A61B 1/015* (2013.01); *A61B 1/018* (2013.01); *A61B 1/04* (2013.01); *A61B 1/06* (2013.01); *G02B 23/2476* (2013.01); *G03B 17/08* (2013.01); *G03B 37/005* (2013.01)

(56) References Cited

U.S. PATENT DOCUMENTS

| | | | |
|---|---|---|---|
| 2012/0053414 A1* | 3/2012 | Arai | F16J 15/025 600/121 |
| 2013/0236208 A1* | 9/2013 | Komatsu | G03G 15/161 399/101 |
| 2015/0164313 A1* | 6/2015 | Ouyang | A61B 1/00103 600/103 |

* cited by examiner

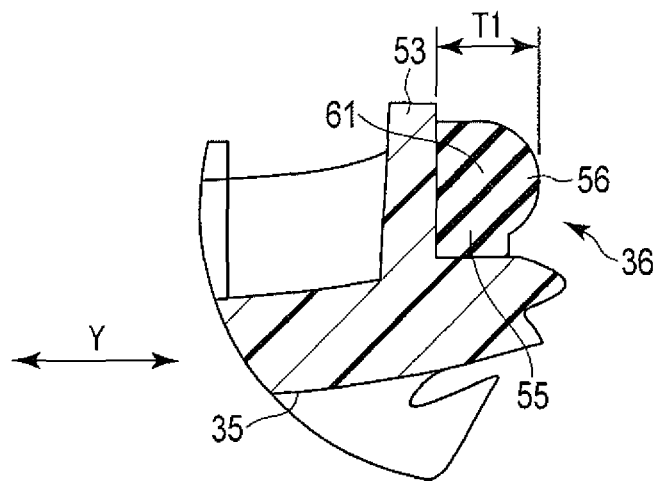
F I G. 4
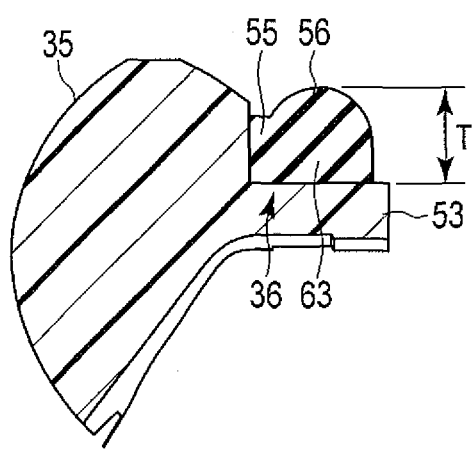
F I G. 5

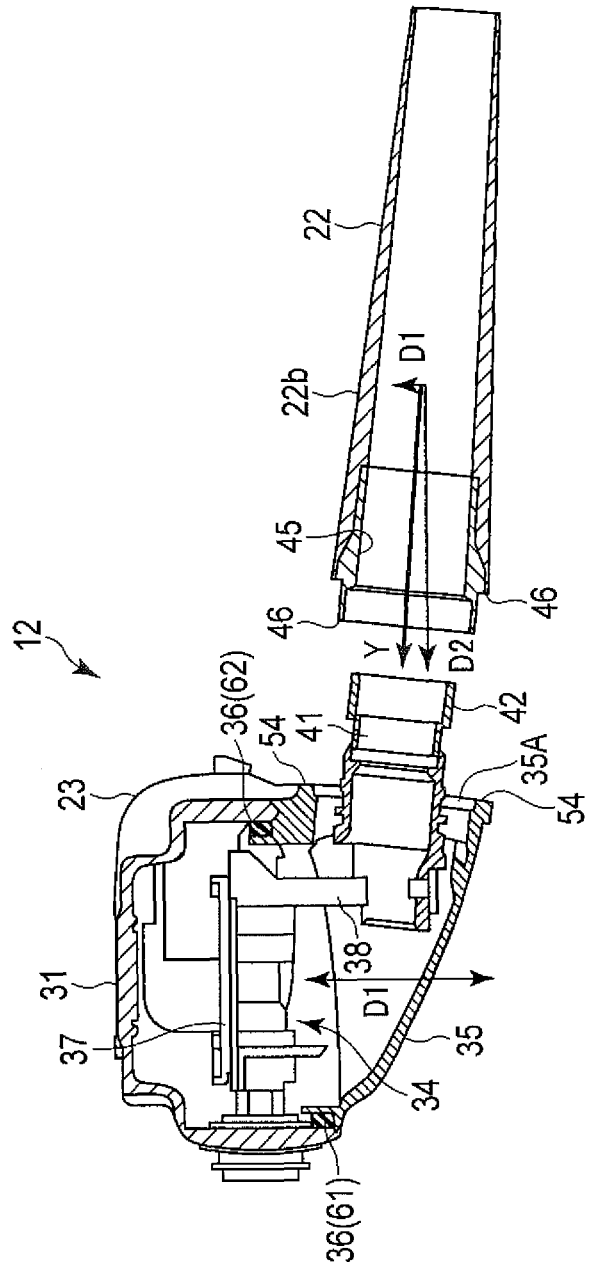
F I G. 8

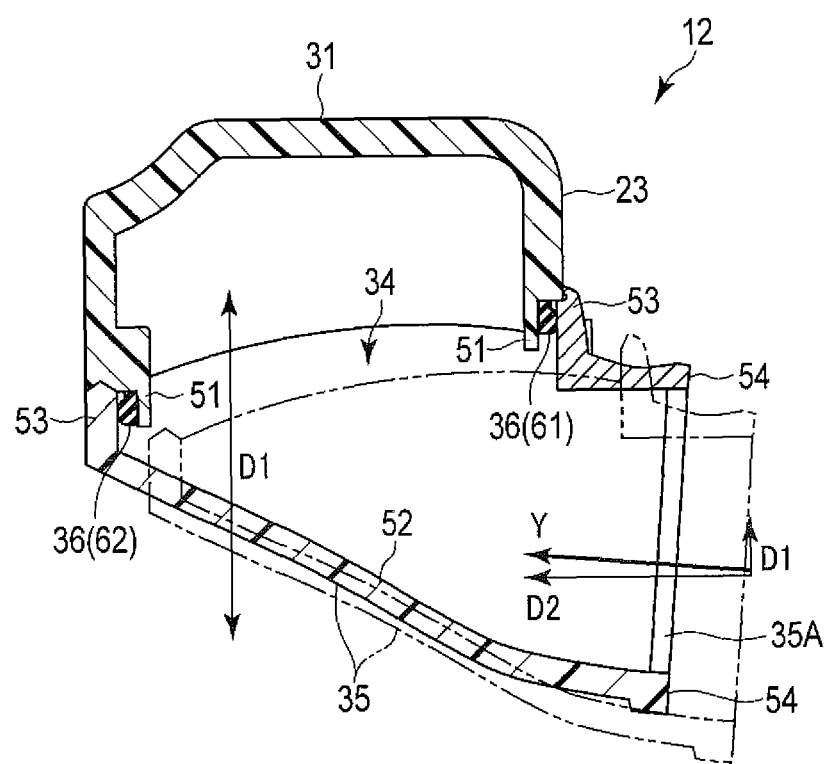
F I G. 12

HOUSING WATERTIGHT MECHANISM AND ENDOSCOPE

CROSS-REFERENCE TO RELATED APPLICATIONS

This application is a Continuation application of PCT Application No. PCT/JP2015/073384, filed Aug. 20, 2015 and based upon and claiming the benefit of priority from prior Japanese Patent Application No. 2014-169772, filed Aug. 22, 2014, the entire contents of all of which are incorporated herein by reference.

BACKGROUND OF THE INVENTION

1. Field of the Invention

The present invention relates to a housing watertight mechanism used for an introducing device inserted into a cavity.

2. Description of the Related Art

Jpn. Pat. Appln. KOKAI Publication No. 2012-47884 discloses introducing devices inserted into a cavity, such as an endoscope, for example, include a flexible inserting unit inserted into a subject to observe and treat a lesioned part in the subject, and an operating unit (housing) performing an operation to bend the inserting unit in a predetermined direction.

A waterproof case of the operating unit includes a case main body, a cover member, and an annular lip packing. The attachment direction in attaching the cover member to the case main body is inclined with respect to a direction facing an opening portion of the case main body.

CITATION LIST

Patent Literature 1: Japanese Patent Application Publication No. 2012-47884

BRIEF SUMMARY OF THE INVENTION

A housing watertight mechanism according to an embodiment of the present invention comprises: a case member including a first edge portion defining a circumference of an opening portion; a lid member disposed to cover the opening portion, including a second edge portion opposed to the first edge portion, and configured to be fixed to the case member in an attaching and detaching direction inclined with respect to a direction passing through the opening portion, an annular elastic member interposed between the first edge portion and the second edge portion, and compressed in the attaching and detaching direction to fill a space between the first edge portion and the second edge portion when the lid member is fixed to the case member, a first portion formed in the elastic member and disposed on a side on which the space between the first edge portion and the second edge portion is narrowed when the elastic member is compressed in the attaching and detaching direction, and a second portion formed in the elastic member, disposed on a side on which the space between the first edge portion and the second edge portion is broadened when the elastic member is compressed in the attaching and detaching direction, and having a larger size in the attaching and detaching direction than a size of the first portion in the attaching and detaching direction.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4 is a cross-sectional view taken along line F4-F4 illustrated in FIG. 3;

FIG. 5 is a cross-sectional view taken along line F5-F5 illustrated in FIG. 3;

FIG. 8 is a cross-sectional view illustrating the operating unit and thereareound of the endoscope illustrated in FIG. 2, by cutting it with a plane extending through the central axis thereof;

FIG. 12 is a cross-sectional view illustrating a step of attaching a lid member to a case member in an operating unit of an endoscope apparatus according to a second embodiment;

DETAILED DESCRIPTION OF THE INVENTION

First Embodiment

Figure 1:
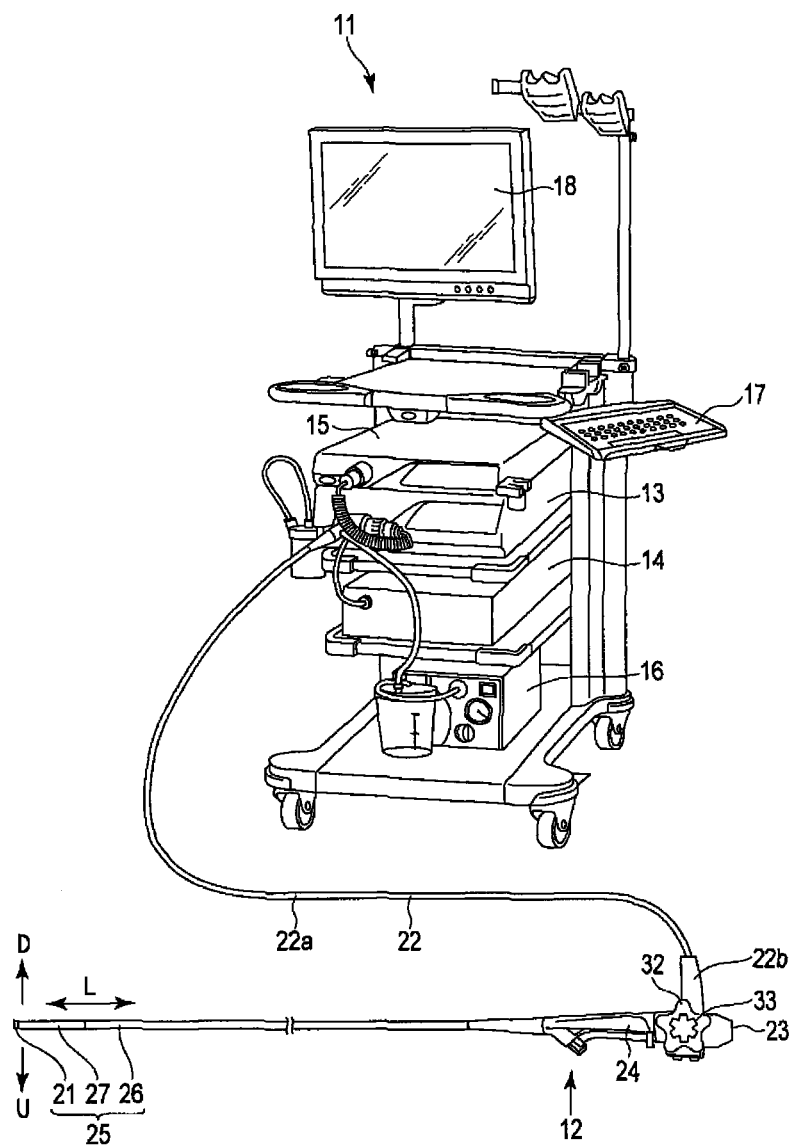
FIG. 1 is a perspective view illustrating a whole structure of an endoscope apparatus according to a first embodiment.
Figure 2:
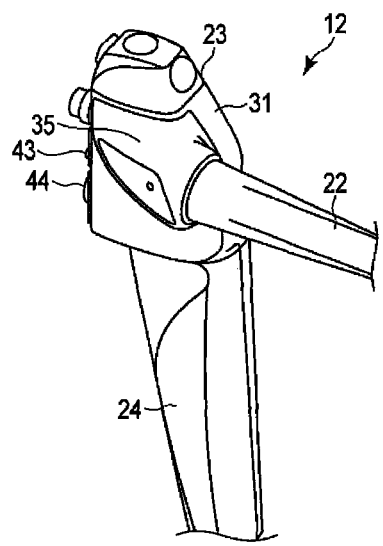
FIG. 2 is a perspective view illustrating a case member and a lid member of an operating unit of an endoscope in the endoscope apparatus illustrated in FIG. 1.

FIG. 1 is a diagram illustrating a whole structure of an endoscope apparatus according to the present invention. As illustrated in FIG. 1, an endoscope apparatus 11 includes an endoscope 12, a controller 13, a light source device 14, an imaging device 15, an air/water feed and suction device 16, a keyboard 17, and a monitor 18.

The light source device 14 supplies light to an illumination lens disposed in a distal end hard portion 21 of the endoscope 12 described later, under the control of the controller 13. The air/water feed and suction device 16 feeds air and/or water to a nozzle disposed in the distal end hard portion 21 of the endoscope 12, under the control of the controller 13, and sucks liquid and/or tissue from the inside of the living body via the nozzle. The imaging device 15 performs image processing on an image of a subject that is photographed through an objective lens of the distal end hard portion 21 of the endoscope 12, and displays the image on the monitor 18, under the control of the controller 13.

As illustrated in FIG. 1, the endoscope 12 includes a universal cord 22, an operating unit 23, a grip unit 24 adjacent to the operating unit 23 and provided as one unitary piece with the operating unit 23, and an inserting unit 25 extending from the grip unit 24 and inserted into a cavity (subject). The universal cord 22 includes a flexible cable 22a, and a bend stopper 22b preventing an abrupt bend or buckle of the cable 22a. The operating unit 23 is an example of a housing to which the watertight mechanism is applied.

The endoscope 12 is connected with the controller 13, the light source device 14, the imaging device 15, and the air/water feed and suction device 16, via the universal cord 22.

The inserting unit 25 includes a soft portion 26 that is elongated and has flexibility, a bending portion 27 provided at a distal end of the soft portion 26, and the distal end hard portion 21 provided at a distal end of the bending portion 27.

A pair of first wires to bend the bending portion 27 in a U direction and a D direction illustrated in FIG. 1, and a pair of second wires to bend the bending portion 27 in a R direction and a L direction orthogonal to the U direction and the D direction are inserted through the inside of the soft portion 26 and the bending portion 27. A plurality of bending pieces are contained inside the bending portion 27. The bending pieces are arranged along the longitudinal axis direction L of the inserting unit 25. The distal end hard portion 21 is provided with the objective lens, a treatment tool inserting channel, the illumination lens, and the nozzle capable of supplying water and/or air to wash the distal end surface of the distal end hard portion 21 and sucking liquid and/or tissue inside the living body.

As illustrated in FIG. 1 to FIG. 3 and FIG. 8, the operating unit 23 includes a case member 31 formed of a synthetic resin material or the like to have an internal space, a UD knob 32 and a RL knob 33 that are rotatably attached to the case member 31, a lid member 35 to cover an opening portion 34 provided in the case member 31, an annular elastic member 36 interposed between the case member 31 and the lid member 35, a metal plate-shaped frame 37 contained in the case member 31, a metal supporting portion 38 projecting in an arm shape from the frame 37, a cylindrical metal fixing portion 41 attached to the supporting portion 38, a first screw portion 42 (male screw) provided around the fixing portion 41, a first button 43 to perform air feed and/or water feed to the nozzle of the distal end hard portion 21, and a second button 44 to perform suction with the distal end hard portion 21 via the nozzle. The fixing portion 41 projects from the case member 31, and is provided to extend through a hole portion 35a provided in the lid member 35.

As illustrated in FIG. 8, the bend stopper 22b of the universal cord 22 extends along an attaching and detaching direction Y of the lid member 35. An end portion of the bend stopper 22b of the universal cord 22 is provided with a second screw portion 45 (female screw) engaged with the first screw portion 42, and an abutment portion 46 abutting against the lid member 35 when it is fixed to the fixing portion 41. The bend stopper 22b of the universal cord 22 is fixed to the fixing portion 41 to press down the lid member 35, and also serves as a fixing tool for the lid member 35. The universal cord 22 is an example of the cable member.

Figure 3:
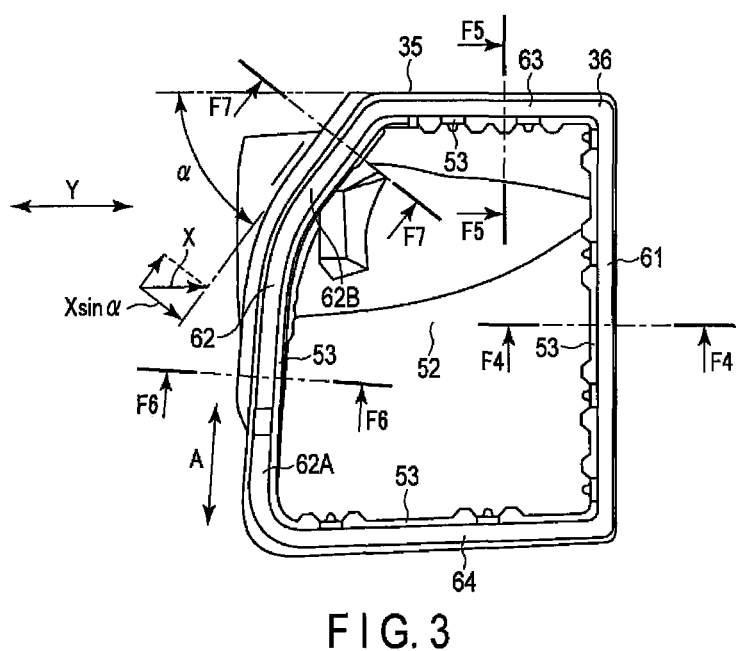
FIG. 3 is a front view illustrating an inside of the lid member of the operating unit illustrated in FIG. 2.
Figure 9:
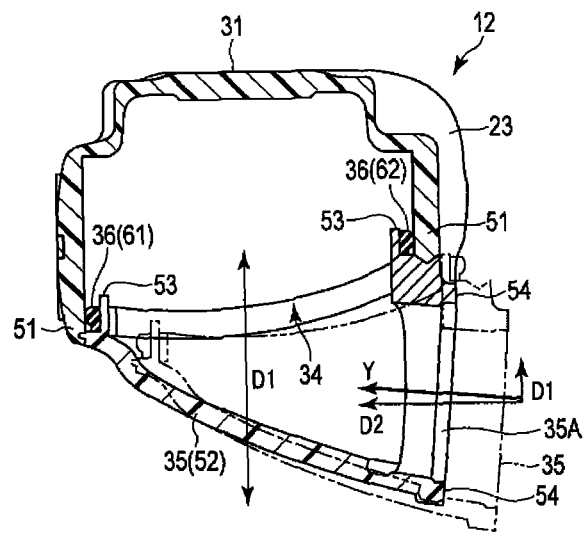
FIG. 9 is a cross-sectional view illustrating a step of attaching the lid member to the case member of the operating unit illustrated in FIG. 8.

As illustrated in FIG. 9, the case member 31 and the lid member 35 are formed of, for example, a synthetic resin material. The case member 31 includes a first edge portion 51 defining the circumference of the opening portion 34. The lid member 35 includes a main body portion 52, a second edge portion 53 projecting from the main body portion 52 toward the case member 31, a hole portion 35A provided in the main body portion 52, and a receiving portion 54 provided around the hole portion 35A and against which the abutment portion 46 abuts. As illustrated in FIG. 3, the second edge portion 53 has an annular shape, and is opposed to the first edge portion 51 in the state where the lid member 35 covers the opening portion 34. As illustrated in FIG. 9, the lid member 35 is capable of covering the opening portion 34 and is detachable from the opening portion 34, along the attaching and detaching direction Y inclined with respect to the direction passing through the opening portion 34. The frame 37 is formed of, for example, a metal material and in a plate shape.

As illustrated in FIG. 9, the elastic member 36 is formed as one unitary piece with the second edge portion 53 of the lid member 35. The elastic member 36 is interposed between the first edge portion 51 and the second edge portion 53. When the lid member 35 covers the opening portion 34, the elastic member 36 is compressed in the detaching direction Y, and capable of covering the space between the first edge portion 51 and the second edge portion 53. The elastic member 36 is formed of, for example, silicon rubber. The elastic member 36 includes a base portion 55 fixed to the second edge portion 53, and a contact portion 56 projecting in a semicircular shape from the base portion 55 and capable of contacting the first edge portion 51.

As illustrated in FIG. 3, the elastic member 36 includes a first portion 61 disposed on a side of a direction (left side in FIG. 9) approaching the case member 31 in the attaching and detaching direction Y, a second portion 62 disposed on a side of a direction (right side in FIG. 9) going away from the case member 31 in the attaching and detaching direction Y, a third portion 63 connecting the first portion 61 with the second portion 62 and forming a short side, and a fourth portion 64 connecting the first portion 61 with the second portion 62 and forming a long side. With the structure, the elastic member 36 can be regarded as having a substantially polygonal annular shape. In addition, the second portion 62 includes a main body portion 62A extending in a direction A crossing the attaching and detaching direction Y of the case member 31 and running along the lid member 35, and an inclined portion 62B inclined with respect to the main body portion 62A and running along the lid member 35.

Figure 6:
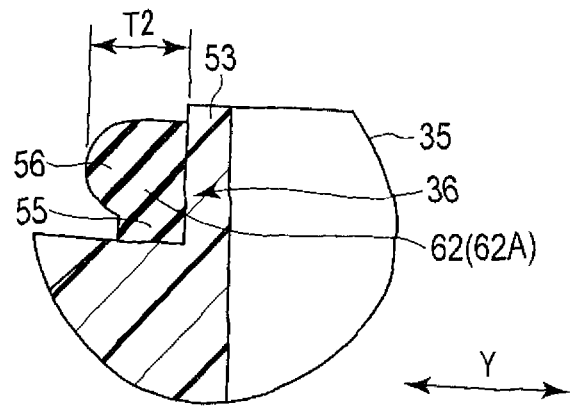
FIG. 6 is a cross-sectional view taken along line F6-F6 illustrated in FIG. 3.
Figure 7:
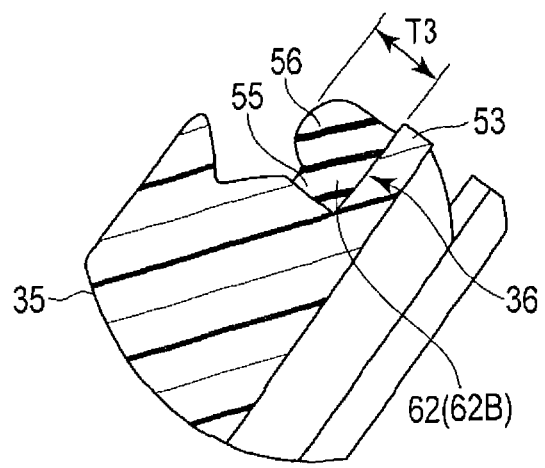
FIG. 7 is a cross-sectional view taken along line F7-F7 illustrated in FIG. 3.

As illustrated in FIG. 6, for example, the main body portion 62A of the second portion 62 has a size T2 in the detaching direction Y. As illustrated in FIG. 7, the inclined portion 62B of the second portion 62 has a height T3 in a direction crossing the inclined portion 62B. As illustrated in FIG. 4, the first portion 61 has a size T1 in the attaching and detaching direction Y. As illustrated in FIG. 5, the third portion 63 has, for example, a height T. In the same manner, although illustration of the fourth portion 64 is omitted, the fourth portion 64 has, for example, the height T. In the present embodiment, "T=T1<T3<T2" is satisfied. More specifically, the size T is, for example, 1.8 mm to 2.0 mm, the size T3 is, for example, 2.1 mm to 2.2 mm, and the size T2 is, for example, 2.3 mm to 2.4 mm.

The size T2 of the main body portion of the second portion 62 and the size T3 of the inclined portion 62B can be properly set within a range of a size larger than the size T1 of the first portion 61 and not exceeding twice as large as the size T1 of the first portion 61. The sizes of the first portion 61 to the fourth portion 64 can be calculated by simulation based on the magnitude and the direction (angle) of the force applied on the portions.

The following is explanation of the work process in fixing the lid member 35 to the case member 31, with reference to FIG. 8 to FIG. 11. As illustrated in FIG. 8, the lid member 35 is caused to cover the opening portion 34 of the case member 31, and the fixing portion 41 is inserted into the hole portion 35A of the lid member 35. Thereafter, after the cable 22a that is not illustrated is fixed to the fixing portion 41, the second screw portion 45 of the bend stopper 22b is fixed to the first screw portion 42 of the fixing portion 41. In the fixing, when the bend stopper 22b is fixed to the fixing portion 41 on the operating unit 23 side while the bend stopper 22b is rotated around the central axis thereof, the bend stopper 22b approaches the operating unit 23 along the attaching and detaching direction Y inclined with respect to the direction passing through the opening portion 34, as illustrated in FIG. 8. Then, the abutment portion 46 of the bend stopper 22b abuts against the receiving portion 54 of the lid member 35, and the lid member 35 is pushed in, together with the bend stopper 22b, along the detaching direction Y, as illustrated in FIG. 9. In this operation, as illustrated in FIG. 8, components of the vector in the moving direction (detaching direction Y) of the lid member 35 include both a component in the direction D1 passing through the opening portion 34 and a component in the direction D2 crossing (substantially orthogonal to) the direction D1.

Figure 10:
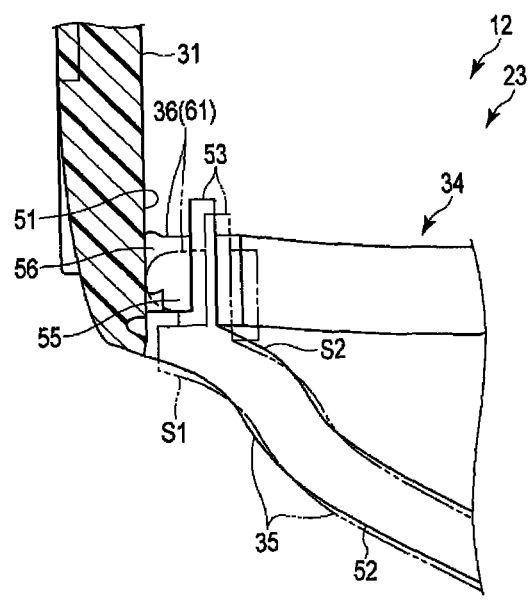
FIG. 10 is an enlarged cross-sectional view of a first portion and thereareound of an elastic member in the step of attaching the lid member illustrated in FIG. 9.

In FIG. 10, two-dot chain lines indicate a first state S1 directly before the elastic member 36 is compressed (pushed in by the bend stopper 22b) in the attaching and detaching direction Y in a portion around the first portion 61 of the elastic member 36, and solid lines indicate a second state S2 in which the elastic member 36 is compressed (pushed in by the bend stopper 22b) in the attaching and detaching direction Y. In the portion around the first portion 61, when the lid member 35 is moved from the first state S1 to the second state S2, the space between the first edge portion 51 and the second edge portion 53 is narrowed. With the structure, the first portion 61 is enabled to exert sufficient contact pressure on the first edge portion 51.

Figure 11:
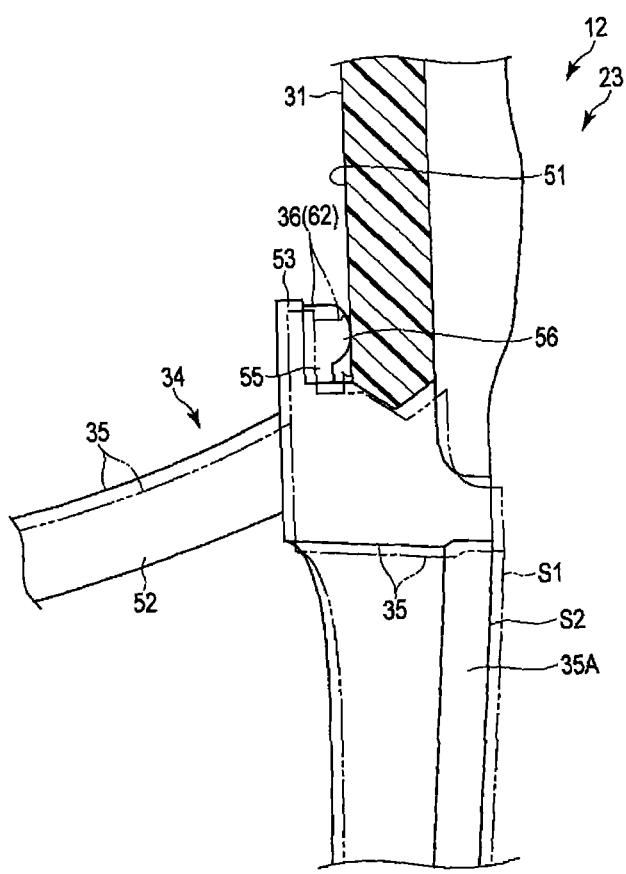
FIG. 11 is an enlarged cross-sectional view of a second portion and thereareound of the elastic member in the step of attaching the lid member illustrated in FIG. 9.

In FIG. 11, two-dot chain lines indicate a first state S1 directly before the elastic member 36 is compressed (pushed in by the bend stopper 22b) in the attaching and detaching direction Y in a portion around the second portion 62 of the elastic member 36, and solid lines indicate a second state S2 in which the elastic member 36 is compressed (pushed by the bend stopper 22b) in the attaching and detaching direction Y. In the portion around the second portion 62, when the lid member 35 is moved from the first state S1 to the second state S2, the space between the first edge portion 51 and the second edge portion 53 is broadened. However, the size T2 of the main body portion 62A of the second portion 62 in the detaching direction is set larger than the size T1 of the second portion 62. With the structure, the second portion 62 is enabled to exert sufficient contact pressure on the first edge portion 51.

The inclined portion 62B of the second portion 62 will be explained hereinafter with reference to FIG. 3. Supposing that X is a distance by which the lid member 35 moves from the first state S1 to the second state S2 along the attaching and detaching direction Y, the movement distance thereof in a direction (a normal direction of a line segment formed by the inclined portion 62B) crossing the inclined portion 62B of the second portion 62 is $X \sin \alpha$. For this reason, the movement distance in the direction crossing the inclined portion 62B of the second portion 62 is smaller than the distance by which the lid member 35 is moved in the attaching and detaching direction Y. In addition, around the inclined portion 62B of the second portion 62, when the lid member 35 is moved from the first state S1 to the second state S2, the space between the first edge portion 51 and the second edge portion 53 is broadened. However, the degree of broadening of the space around the inclined portion 62B is smaller than the degree of broadening around the main body portion 62A. For this reason, the size T3 of the inclined portion 62B in the direction crossing the inclined portion 62B is set larger than the size T1 of the first portion 61, and smaller than the size T2 of the main body portion 62A of the second portion 62. This structure secures sufficient contact pressure in the inclined portion 62g. In the same manner, this structure also secures sufficient contact pressure in the third portion 63 and the fourth portion 64 of the elastic member 36.

According to the first embodiment, the housing watertight mechanism includes the case member 31 including the first edge portion 51 defining the circumference of the opening portion 34, the lid member 35 disposed to cover the opening portion 34, including the second edge portion 53 opposed to the first edge portion 51, and configured to be fixed to the case member 31 in the attaching and detaching direction Y inclined with respect to the direction passing through the opening portion 34, the annular elastic member 36 interposed between the first edge portion 51 and the second edge portion 53, and compressed in the detaching direction Y to fill the space between the first edge portion 51 and the second edge portion 53 when the lid member 35 is fixed to the case member 31, the first portion 61 formed in the elastic member 36 and disposed on the side on which the space between the first edge portion 51 and the second edge portion 53 is narrowed when the elastic member 36 is compressed in the attaching and detaching direction Y, and the second portion 62 formed in the elastic member 36, disposed on the side on which the space between the first edge portion 51 and the second edge portion 53 is broadened when the elastic member 36 is compressed in the attaching and detaching direction Y, and having a larger size in the attaching and detaching direction Y than a size of the first portion 61 in the attaching and detaching direction Y.

This structure prevents reduction in contact pressure of the elastic member 36 in the second portion 62 in which the space between the first edge portion 51 and the second edge portion 53 is broadened in movement from the first state S1 to the second state S2, and prevents water infiltration from the portion.

This structure improves watertightness (waterproofness) of the housing, prevents malfunction caused by water infiltration, and improves the reliability of the introducing device or the like to which the structure is applied.

The first portion 61 is disposed on the side of the direction approaching the case member 31 in the attaching and detaching direction Y, and the second portion 62 is disposed on the side of the direction going away from the case member 31 in the attaching and detaching direction Y. This structure prevents loss of seal in the elastic member 36 on the side of the direction going away from the case member 31 in the attaching and detaching direction Y in which the contact pressure easily decreases, and prevents infiltration of water from the portion.

The housing watertight mechanism includes a cable member inserted through an inside of the case member 31 and the lid member 35, and a fixing portion 41 fixing the cable member to the lid member 35 such that the cable member is caused to extend along the attaching and detaching direction Y and pressing the lid member 35 on the case member 31. Because the lid member 35 is fixed with the cable member, this structure removes the necessity for a separate fixing tool to fix the lid member 35, and reduces the number of components. In addition, this structure also removes the necessity for a hole to let a screw for fixing the lid member 35 extend through, and removes the risk of water infiltration through the hole.

The second portion 62 includes the main body portion 62A that extends in the direction A crossing the attaching and detaching direction Y and running along the lid member 35, and the inclined portion 62B extending in the direction along the lid member 35 and inclined with respect to the main body portion 62A, and a size of the second portion 62 in the direction crossing the inclined portion 62B is larger than the size of the first portion 61 in the attaching and detaching direction Y, and smaller than the size of the main body portion 62A in the detaching direction Y. When the lid member 35 is moved from the first state S1 to the second state S2, the movement amount in the direction crossing the inclined portion 62B is smaller than the movement amount in the attaching and detaching direction Y. This structure enables setting of the size of the inclined portion 62B in the direction crossing the inclined portion 62B within a proper range, and prevents occurrence of loss in seal (water infiltration) in the inclined portion 62B.

[Modification]

The following is explanation of a modification of the first embodiment. In the modification, unlike the first embodiment, the size and the cross section in the attaching and detaching direction Y are the same between the first portion 61 and the second portion 62. However, in the present modification, the hardness of the elastic member 36 (rubber) is set to different values between the first portion 61 and the second portion 62.

Specifically, the first portion 61 on the side on which a space between the first edge portion 51 and the edge portion 53 is narrowed when the elastic member 36 is compressed in the attaching and detaching direction Y has hardness (solidity) lower than hardness of the second portion 62. Specifically, the hardness of the first portion 61 is adjusted to, for example, 50 degrees as hardness measured with a type A durometer for ordinary rubber (medium hardness) compliant with the standard such as ISO 7619 and JIS K 6253. The second portion 62 on the side on which a space between the first edge portion 51 and the edge portion 53 is broadened when the elastic member 36 is compressed in the attaching and detaching direction Y has hardness (solidity) higher than hardness of the first portion 61. Specifically, the hardness of the first portion 61 is adjusted to, for example, 60 degrees as hardness measured with the type A durometer.

According to the present modification, the hardness of the second portion 62 is set higher than the hardness of the first portion 61. This structure prevents occurrence of water infiltration around the second portion 62 of the elastic member 36. This structure improves the reliability of the introducing device to which the housing watertight structure is applied.

Second Embodiment

An endoscope apparatus according to a second embodiment will be explained hereinafter with reference to FIG. 13 and FIG. 14. An endoscope apparatus 11 according to the second embodiment is different from that of the first embodiment in shape of the case member 31 and shape of the lid member 35, but the other parts are the same as those of the first embodiment. Therefore, the part different from the first embodiment will be mainly explained, and illustration or explanation of the parts that are the same as those of the first embodiment is omitted.

The case member 31 and the lid member 35 are formed of, for example, a synthetic resin material. The case member 31 includes a first edge portion 51 defining the circumference of the opening portion 34. The first edge portion 51 projects toward a direction in which the lid member 35 exists.

The lid member 35 includes a main body portion 52, a second edge portion 53 projecting from the main body portion 52 toward the case member 31, a hole portion 35A provided in the main body portion 52, and a receiving portion 54 provided around the hole portion 35A and against which the abutment portion 46 abuts. The second edge portion 53 has an annular shape, and is opposed to the first edge portion 51 in the state where the lid member 35 covers the opening portion 34. The second edge portion 53 is disposed outside the first edge portion 51, in the state where the lid member 35 covers the opening portion 34. The lid member 35 is capable of covering the opening portion 34 and is detachable from the opening portion 34, along the attaching and detaching direction Y. A fixing portion 41 extending from the internal direction of the case member 31 is inserted through the inside of the hole portion 35A. A frame 37 is formed of, for example, a metal plate.

An elastic member 36 has an annular shape, in the same manner as the first embodiment. In the present embodiment, the elastic member 36 is formed as one unitary piece with the first edge portion 51 of the case member 31. The elastic member 36 is formed of, for example, silicon rubber. The elastic member 36 includes a base portion 55 fixed to the first edge portion 51, and a contact portion 56 projecting in a semicircular shape from the base portion 55 and capable of abutting against the second edge portion 53.

The elastic member 36 includes a first portion 61 disposed on a side of a direction (right side in FIG. 13) going away from the case member 31 in the attaching and detaching direction Y, a second portion 62 disposed on a side of a direction (left side in FIG. 13) approaching the case member 31 in the attaching and detaching direction Y, a third portion 63 connecting the first portion 61 with the second portion 62 and forming a short side, and a fourth portion 64 connecting the first portion 61 with the second portion 62 and forming a long side. The second portion 62 includes a main body portion 62A extending in a direction crossing the attaching and detaching direction Y of the case member 31, and an inclined portion 62B inclined with respect to the main body portion 62A and the attaching and detaching direction Y.

In the same manner as the first embodiment, for example, the main body portion 62A of the second portion 62 has a size T2 in the detaching direction Y. The inclined portion 62B of the second portion 62 has a height T3 in a direction crossing the inclined portion 62B, for example. The first portion 61 has a size T1 in the detaching direction Y. The third portion 63 has, for example, a height T. The fourth portion 64 has, for example, the height T. In the present embodiment, "T=T1<T3<T2" is satisfied. More specifically, the size T is, for example, 1.8 mm to 2.0 mm, the size T3 is, for example, 2.1 mm to 2.2 mm, and the size T2 is, for example, 2.3 mm to 2.4 mm. The size T2 of the main body portion 62A of the second portion 62 and the size T3 of the inclined portion 62B can be properly set within a range of a size larger than the size T1 of the first portion 61 and not exceeding twice as large as the size T1 of the first portion 61.

Figure 13:
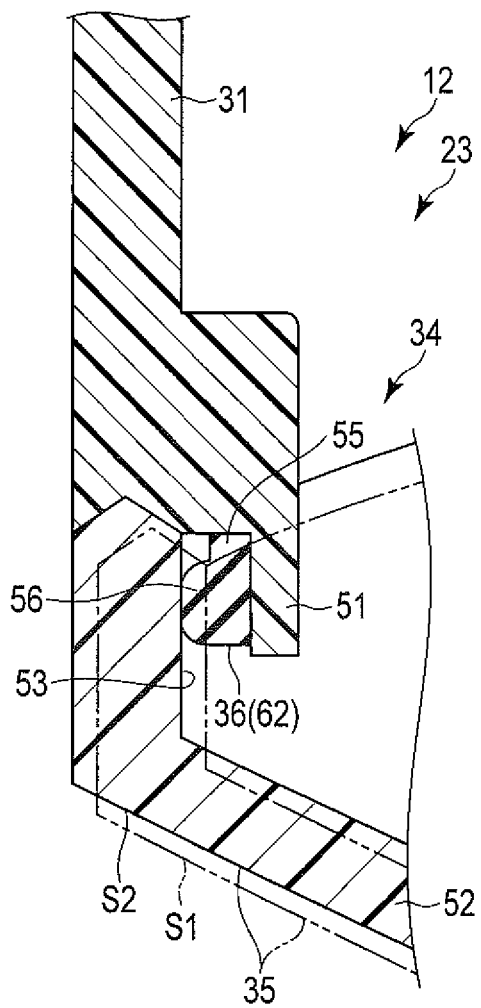
FIG. 13 is an enlarged cross-sectional view of a second portion and thereareound of an elastic member in the step of attaching the lid member illustrated in FIG. 12.
Figure 14:
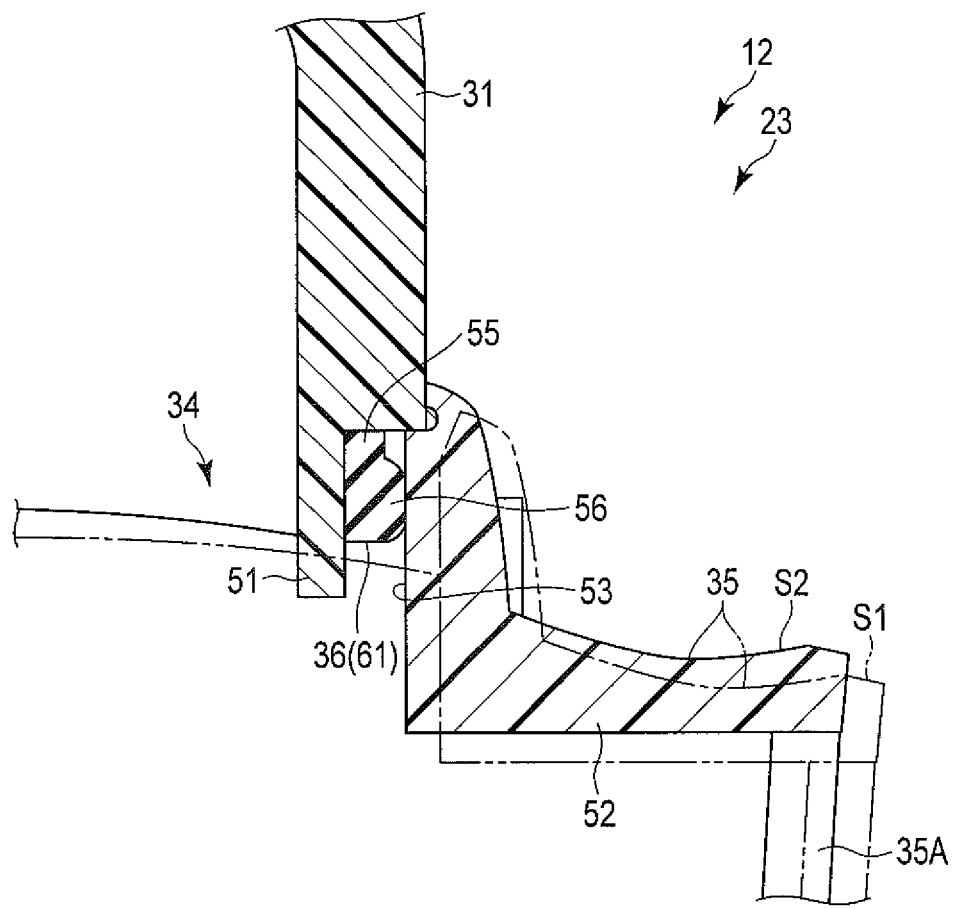
FIG. 14 is an enlarged cross-sectional view of a first portion and thereareound of the elastic member in the step of attaching the lid member illustrated in FIG. 12.

The following is explanation of the work process in covering the opening portion 34 (first edge portion 51) of the case member 31 with the lid member 35, with reference to FIG. 13 and FIG. 14. First, the first portion 41 is inserted into the hole portion 35A of the lid member 35 in advance. Thereafter, after the cable 22a that is not illustrated is fixed to the fixing portion 41, the second screw portion 45 of the bend stopper 22b is fixed to the first screw portion 42 of the fixing portion 41. In the fixing, when the bend stopper 22b is fixed to the fixing portion 41 on the operating unit 23 side while the bend stopper 22b is rotated, the bend stopper 22b approaches the operating unit 23 along the attaching and detaching direction Y inclined with respect to the direction D1 passing through the opening portion 34, as illustrated in FIG. 13. Then, the abutment portion 46 of the bend stopper 22b abuts against the receiving portion 54 of the lid member 35, and the lid member 35 is pushed in, together with the bend stopper 22b, along the attaching and detaching direction Y. In this operation, as illustrated in FIG. 13, components of the vector in the moving direction (attaching and detaching direction Y) of the lid member 35 include both a component in the direction D1 passing through the opening portion 34 and a component in the direction D2 crossing (substantially orthogonal to) the direction D1.

In FIG. 13, two-dot chain lines indicate a first state S1 directly before the elastic member 36 is compressed (pushed in by the bend stopper 22b) in the attaching and detaching direction Y in a portion around the second portion 62 of the elastic member 36, and solid lines indicate a second state S2 in which the elastic member 36 is compressed (pushed in by the bend stopper 22b) in the attaching and detaching direction Y. In the portion around the second portion 62, when the lid member 35 is moved from the first state S1 to the second state S2, the space between the first edge portion 51 and the second edge portion 53 is broadened. However, the size T2 of the main body portion 62A of the second portion 62 in the attaching and detaching direction Y is set larger than the size T1 of the first portion 61. With the structure, the second portion 62 is enabled to exert sufficient contact pressure on the second edge portion 53. The same is applicable in the inclined portion 62B of the second portion 62.

In FIG. 14, two-dot chain lines indicate a first state S1 directly before the elastic member 36 is compressed (pushed in by the bend stopper 22b) in the attaching and detaching direction Y in a portion around the first portion 61 of the elastic member 36, and solid lines indicate a second state S2 in which the elastic member 36 is compressed (pushed in by the bend stopper 22b) in the attaching and detaching direction Y. In the portion around the first portion 61, when the lid member 35 is moved from the first state S1 to the second state S2, the space between the first edge portion 51 and the second edge portion 53 is narrowed. With the structure, the first portion 61 is enabled to exert sufficient contact pressure on the second edge portion 53.

The second embodiment prevents occurrence of water infiltration in the second portion 62 of the elastic member 36 in which the space between the first edge portion 51 and the second edge portion 53 is broadened in movement from the first state S1 to the second state S2, even when the elastic member 36 is fixed to the case member 31 side. This structure improves the reliability of the introducing device to which the housing watertight structure is applied.

The present invention is not limited to the embodiments described above, but may be properly modified and carried out within a range not departing from the gist. In addition, an endoscope apparatus may be made by combining the endoscope apparatuses of the embodiments described above.

Each of the embodiments described above illustrates the operating unit 23 of the endoscope 12, as an example of the housing watertight mechanism. Other examples of the endoscope 12 having the operating unit 23 as described above include a structure including no illumination optical system including the light source device and the illumination lens of the distal end hard portion or the like, and a structure including no observation optical system including the monitor and the objective lens of the distal end hard portion or the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A housing watertight mechanism comprising:
   a case member including a first edge portion defining a circumference of an opening portion;
   a lid member disposed to cover the opening portion, the lid member including a second edge portion opposed to the first edge portion, and the lid member being configured to be fixed to the case member in a attaching and detaching direction inclined with respect to a direction passing through the opening portion;
   an annular elastic member interposed between the first edge portion and the second edge portion, the annular elastic member being compressed in the attaching and detaching direction to fill a space between the first edge portion and the second edge portion when the lid member is fixed to the case member;
   a first portion formed in the elastic member, the first portion being disposed on a side on which the space between the first edge portion and the second edge portion is narrowed when the elastic member is compressed in the attaching and detaching direction; and
   a second portion formed in the elastic member, the second portion being disposed on a side on which the space between the first edge portion and the second edge portion is broadened when the elastic member is compressed in the attaching and detaching direction, and the second portion having a first hardness in an uncompressed state that is higher than a second hardness of the first portion in an uncompressed state.

2. The housing watertight mechanism according to claim 1, wherein
   the first portion is disposed on a side of a direction approaching the case member in the attaching and detaching direction, and the second portion is disposed on a side of a direction going away from the case member in the attaching and detaching direction.

3. An endoscope including the housing watertight mechanism according to claim 2, comprising:
   a cable member inserted through an inside of the case member and the lid member; and
   a fixing portion fixing the cable member to the lid member such that the cable member is caused to extend along the attaching and detaching direction, and pressing the lid member on the case member.

4. The endoscope according to claim 3, wherein
the second portion includes:
- a main body portion extending in a direction crossing the attaching and detaching direction and running along the lid member; and
- an inclined portion extending in the direction running along the lid member, and inclined with respect to the main body portion, and the second portion has a size that is larger in a direction crossing the inclined portion than a size of the first portion in the attaching and detaching direction, and smaller than a size of the main body portion in the attaching and detaching direction.

* * * * *